United States Patent [19]

Gilbert et al.

[11] 4,338,397

[45] Jul. 6, 1982

[54] MATURE PROTEIN SYNTHESIS

[75] Inventors: Walter Gilbert; Karen Talmadge, both of Cambridge, Mass.

[73] Assignee: President and Fellows of Harvard College, Cambridge, Mass.

[21] Appl. No.: 139,225

[22] Filed: Apr. 11, 1980

[51] Int. Cl.³ .............................................. C12P 21/00
[52] U.S. Cl. ....................................... 435/68; 435/70; 435/172; 435/317; 435/253
[58] Field of Search ...................... 435/68, 70, 71, 172, 435/317, 253

[56] References Cited

U.S. PATENT DOCUMENTS 4,082,613  4/1978  Thirumalachar et al. ............ 195/76
4,237,224 12/1980  Cohen et al. .......................... 435/68

FOREIGN PATENT DOCUMENTS 1516458  7/1978  United Kingdom .
1521032  8/1978  United Kingdom .
1565190  4/1980  United Kingdom .
1568047  5/1980  United Kingdom .

OTHER PUBLICATIONS

Villa-Komaroff et al., Proc. Natl. Acad. Sci. U.S.A., vol. 75, pp. 3727-3731, Aug. 1978.
Sutcliffe, Proc. Natl. Acad. Sci. U.S.A., vol. 75, pp. 3737-3741, Aug. 1978.
Roberts et al., Methods in Enzymology, vol. 68, pp. 473-483, (1979).
Morgan et al., Recombinant DNA and Genetic Experimentation, Pergamon Press, pp. 123-128, (1979).

U.S. Patent Application Ser. Nos. 913,533, filed 6/8/1978; 933,035, filed 8/11/1978.
Goeddel et al., "Direct Expression in *Escherichia coli* of a DNA Sequence Coding for Human Growth Hormone", *Nature*, 281, pp. 544-548, (1979).
Derynck et al., "Expression of Human Fibroblast Interferon Gene in *Escherichia coli*", *Nature*, 287, pp. 193-197, (Sep. 18, 1980).

*Primary Examiner*—Alvin E. Tanenholtz
*Attorney, Agent, or Firm*—Ronald A. Schapira

[57] ABSTRACT

A method is provided for synthesizing within a bacterial host, and secreting through the membrane of the host, a selected mature protein or polypeptide. The method involves:

(a) cleaving a cloning vehicle to form a cleavage site after a promoter of either (1) a bacterial or phage gene within the cloning vehicle or (2) a DNA fragment of the bacterial or phage gene;

(b) forming a hybrid gene by inserting into the cleavage site a non-bacterial DNA fragment which codes for precursor of the selected protein or polypeptide, including the signal sequence of the selected protein or polypeptide;

(c) transforming the host with the cloning vehicle; and then (d) culturing the transformed host to secrete the selected protein or polypeptide.

By this method, mature proteins or polypeptides can be produced, free of signal sequences or other chemical substituents, such as an f-met, on the proteins or polypeptides.

19 Claims, 5 Drawing Figures

FIGURE 2. pKT241 ECORI-PSTI PENICILLINASE GENE FRAGMENT

```
AATTCTTGAAGACGAAAGGGCCTCGTGATACGCCTATTTTTATAGGTTAATGTCATGATAATAATGGTTTCTTAGACGTCAGGTGGCACT
     GAACTTCTGCTTTCCCGGAGCACTATGCGGATAAAAATATCCAATTACAGTACTATTATTACCAAAGAATCTGCAGTCCACCGTGA
     EcoRI

TTTCGGGGAAATGTGCGCGGAACCCCTATTTGTTTATTTTTCTAAATACATTCAAATATGTATCCGCTCATGAGACAATAACCCTGATAA
AAAGCCCCTTTACACGCGCCTTGGGGATAAACAAATAAAAAGATTATGTAAGTTATACATAGGCGAGTACTCTGTTATTGGGACTATT fMetSerIleGlnHisPheArgValAlaAlaLeuIleProLeuGln
ATGGTTCAATAATATTGAAAAAGGAAGAGTATGAGTATTCAACATTTCCGTGTCGCCCTTATTCCCGTGTCA
TAGGAAGTTATTATAACTTTTTCCTTCTCATACTCATAAGTTGTAAAGGCACAGCGGGAATAAGGCG
                                                                   Pst
```

FIGURE 3. pKT218 *ECORI-PSTI* PENICILLINASE GENE FRAGMENT

```
AATTCTTGAAGACGAAAGGGCCTCGTGATACGCCTATTTTTATAGGTTAATGTCATGATAATAATGGTTTCTTAGACGTCAGGTGGCACT
     GAACTTCTGCTTTCCCGGAGCACTATGCGGATAAAAATATCCAATTACAGTACTATTATTACCAAAGAATCTGCAGTCCACCGTGA
     EcoRI

TTTCGGGGAAATGTGCGCGGAACCCCTATTGTTTATTTTCTAAATACATTCAAATATGTATCCGCTCATGAGACAATAACCCTGATAA
AAAGCCCCTTTACACGCGCCTTGGGGATAAACAATAAAAGATTTATGTAAGTTTATACATAGGCGAGTACTCTGTTATTGGGACTATT fMetSerIleGlnAlaAla
ATGCTTCAATAATATTGAAAAAGGAAGAGTATGAGTATTCAAGCTGCA
TACGAAGTTATTATAACTTTTTCCTTCTCATACTCATAAGTTCG
                                              Pst
```

FIGURE 4. 5' END OF PST-CUT RAT PREPROINSULIN GENE FRAGMENT 19

```
                                              -21                                          ↓+1
(LeuGln)GlyGlyGlyGlyGlyGlyTrpMetArgPheLeuProLeuLeuAlaAlaLeuLeuValLeuTrpGluProLysProAlaGlnAlaPheVal...
         GGGGGGGGGGGGGGTGGATGCGCTTCCTGCCCTGCTGCTTCTGGAGCCCAAGCCTGCCCAGGCTTTGTC...
       ACGTCCCCCCCCCCCCCCCACCTACGCGAAGGACGACGAAGACCTCGGTTCGGACGGGTCCGAAAACAG...
       Pst
```

FIGURE 5. 5' END OF PST-CUT RAT PREPROINSULIN GENE FRAGMENT CB6

```
                           -21                                                             ↓+1
(AlaAla)AlaGlyTrpMetArgPheLeuProLeuLeuAlaAlaLeuLeuValLeuTrpGluProLysProAlaGlnAlaPheVal...
        GCGGGGTGGATGCGCTTACTGCCCTGCTGCTTCTGCCCTGCTGCTTCTGGAGCCCAAGCCTGCCCAGGCTTTGTC...
      ACGTCGCCCCACCTACGCGAATGACGGGACGACGAAGAGACCCTCGGGTTCGGACGGGTCCGAAAACAG...
      Pst
```

MATURE PROTEIN SYNTHESIS

The invention described herein was made in the course of work under a grant or award from the United States Department of Health, Education and Welfare.

BACKGROUND OF THE INVENTION

This invention relates to a method of synthesizing within a bacterial host, and secreting through the membrane of the host, a selected protein or polypeptide, such as a eukaryotic cell protein, e.g., proinsulin, serum albumin, human growth hormone, parathyroid hormone and interferon. This invention particularly relates to a method of obtaining from a bacterial host a mature protein or polypeptide and thereby avoiding the need to treat the protein or polypeptide further to remove the signal sequence of other chemical substituents, such as an f-met (i.e., the formaldehyde group on its first methionine group), which are present on its precursor, as synthesized by the bacterial host.

It is known from Gilbert et al U.S. patent application, Ser. No. 913,533, filed June 8, 1978, and Villa-Komaroff et al, *P.N.A.S.* 75, 3727–3731 (1978) that a selected protein or polypeptide can be synthesized within a bacterial host and excreted through the membrane of the host by:

cleaving a cloning vehicle within its bacterial gene which codes for an extracellular or periplasmic carrier protein or polypeptide;

forming a hybrid gene by inserting into the cleavage site a non-bacterial DNA fragment which codes for the selected protein or polypeptide;

transforming the host with the cloning vehicle; and then culturing the transformed host to secrete the selected protein or polypeptide.

However, the selected proteins and polypeptides, made by this method, have been obtained as fused proteins or polypeptides—the selected protein or polypeptide being fused to the bacterial carrier protein or polypeptide. As a result, additional steps have been required to cleave the selected protein or polypeptide from the bacterial carrier protein or polypeptide in order to obtain the selected protein or polypeptide, free of the bacterial carrier protein or polypeptide.

One method proposed to eliminate the fused bacterial carrier protein or polypeptide is to clone the codon for an unusual amino acid directly in front of the non-bacterial DNA fragment for the selected protein or polypeptide and to subject the selected protein or polypeptide, as produced by a transformed host, to chemical cleavage of the unusual amino acid. Itakura, et al, *Science* 198, 1056—1063 (1977). However, besides requiring additional steps to obtain the selected protein or polypeptide, free of the unusual amino acid, this method cannot be used to produce a selected protein or polypeptide containing the unusual amino acid. This is because such a protein or polypeptide would be destroyed by the chemical cleavage of that unusual amino acid.

Another alternative method, that has been proposed, has involved trimming back the DNA of the bacterial gene, so that the non-bacterial DNA fragment is directly after the translational start signal (ATG) of the bacterial DNA. However, this method produces in bacterial hosts the selected protein or polypeptide with an f-met, requiring further steps to obtain just the selected mature protein or polypeptide.

SUMMARY OF THE INVENTION

In accordance with this invention, a method is provided for synthesizing within a bacterial host, and secreting through the membrane of the host, a selected mature protein or polypeptide which comprises:

(a) cleaving a cloning vehicle to form a cleavage site after a promoter of either (1) a bacterial or phage gene within the cloning vehicle or (2) a DNA fragment of the bacterial or phage gene;

(b) forming a hybrid gene by inserting into the cleavage site a non-bacterial DNA fragment which codes for a precursor of the selected protein or polypeptide, including the signal sequence of the selected protein or polypeptide;

(c) transforming the host with the cloning vehicle; and then (d) culturing the transformed host to secrete the selected protein or polypeptide.

By this method, mature proteins or polypeptides can be produced, free of signal sequences or other chemical substituents, such as an f-met, on the proteins or polypeptides. In this regard, the proteins or polypeptides can be recovered either from the periplasmic space of the bacterial host cell or from the medium, in which the host is cultured, depending on the size of the proteins or polypeptides.

BRIEF DESCRIPTION OF THE DRAWINGS

FIG. 2 shows the complete base sequence for a DNA fragment (pKT 241) of the *E. coli* penicillinase gene, after its EcoRI restriction site, containing at its 3' end an inserted Pst restriction site (shown as it apprears after cutting with PstI). FIG. 2 also shows the corresponding amino acid sequence for which this DNA fragment codes. The closest identifiable promoter for this DNA fragment is located in the region 14 to 20 nucleotides before its translational start signal. Sutcliffe, P.N.A.S. 75, 3737–3741 (1978). In the Examples, the 3' end of the *E. coli* DNA fragment (pKT 241) was attached to the signal DNA sequence of the DNA fragment (19) for rat preproinsulin of FIG. 4.

FIG. 3 shows the complete base sequence for another DNA fragment (pKT 218) of the *E. coli* penicillinase gene, after its EcoRI restriction site, containing at its 3' end an inserted Pst restriction site (shown as it appears after cutting with PstI). FIG. 3 also shows the corresponding amino acid sequence for which this DNA fragment codes. The closest identifiable promoter for this DNA fragment is located in the region 14 to 20 nucleotides before its translational start signal. Sutcliffe, supra. In the Examples, the 3' end of this *E. coli* DNA fragment (pKT 218) was attached to the signal DNA sequence of the DNA fragment (CB6) for rat preproinsulin of FIG. 5.

FIG. 4 shows the complete base sequence for the signal DNA sequence of a DNA fragment (19) for rat preproinsulin, containing at its 5' end an inserted Pst restriction site (shown as it appears after cutting with PstI). FIG. 4 also shows the corresponding amino acid sequence for which the signal DNA sequence codes. The signal DNA sequence is from the −21 position to the −1 position of this DNA fragment, and the structural DNA sequence starts at the +1 position of this DNA fragment. In the Examples, the 5' end of this DNA fragment (19) for rat preproinsulin was attached to the *E. coli* DNA fragment (pKT 241) of FIG. 2.

FIG. 5 shows the complete base sequence for the signal DNA sequence of another DNA fragment (CB6) for rat proproinsulin, containing at its 5' end an inserted Pst restriction site (shown as it appears after cutting with PstI). This Figure also shows the corresponding amino acid sequence for which the signal DNA sequence codes. The signal DNA sequence is from the −21 position to the −1 position of this DNA fragment for rat preproinsulin, and the structural DNA sequence starts at the +1 position of this DNA fragment. In the Examples, the 5' end of this DNA fragment (CB6) for rat preproinsulin was attached to the *E. coli* DNA fragment (pKT 218) of FIG. 3.

DETAILED DESCRIPTION OF THE PREFERRED EMBODIMENT

Figure 1:
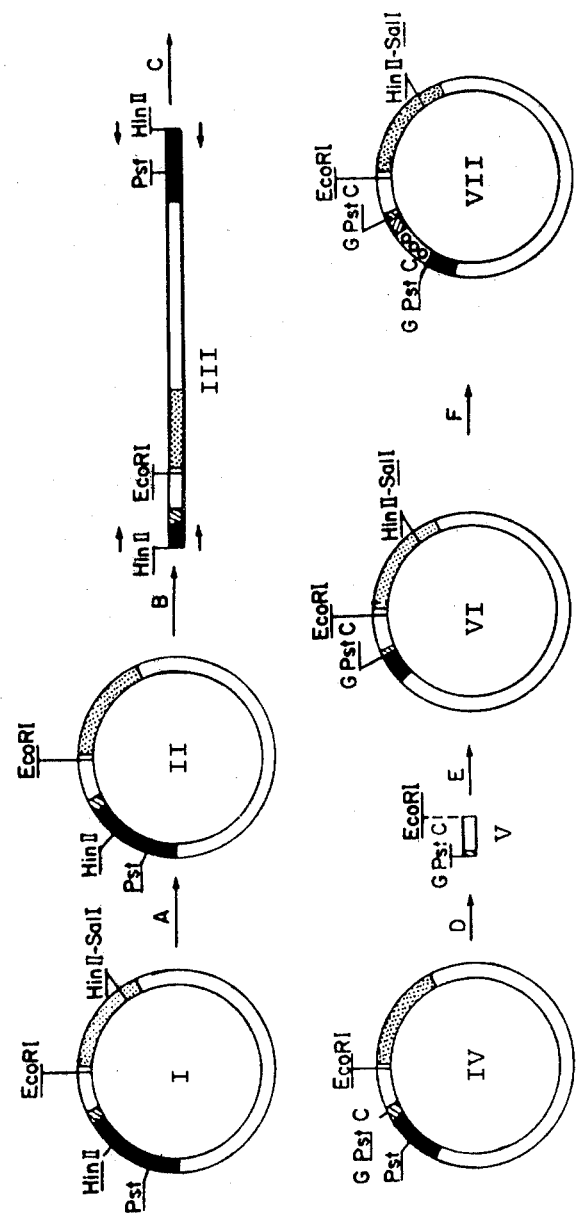
FIG. 1 schematically shows the method, used in the Examples, for inserting a DNA fragment, which codes for rat preproinsulin, into a cloning vehicle made from the plasmid pBR322 and containing a DNA fragment of the *E. coli* penicillinase gene.

In accordance with this detailed description, the following definitions apply:

Protein—A polypeptide containing a linear series of more than fifty amino acids, e.g., proinsulin, serum albumin, human growth hormone, parathyroid hormone, and interferon.

Polypeptide—A linear series of amino acids connected one to the other by peptide bonds between the amino and carboxy groups of adjacent amino acids.

Precursor of a Protein or Polypeptide—A polypeptide or protein as synthesized within a host cell with a signal sequence, e.g., preproinsulin, preserum albumin, prehuman growth hormone, preparathyroid hormone, and preinterferon. In accordance with this invention, a mature polypeptide or protein is secreted through a host's cell membrane with the attendant loss or clipping of the signal sequence of its precursor.

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U").

DNA Sequence—A linear series of nucleotides connected one to the other by phosphodiester bonds between the 3' and 5' carbons of adjacent pentoses.

Codon—A DNA sequence of three nucleotides (a triplet) which encodes through messenger RNA ("mRNA") an amino acid, a translational start signal or a translational termination signal. For example, the nucleotide triplets TTA, TTG, CTT, CTC, CTA and CTG encode for the amino acid leucine ("Leu"), TAG, TAA and TGA are translational stop signals and ATG is a translational start signal.

Plasmid—A non-chromosomal double-stranded DNA sequence comprising an intact "replicon" such that the plasmid is replicated in a host cell. When the plasmid is placed within a unicellular host organism, the characteristics of that organism are changed or transformed as a result of the DNA of the plasmid. For example, a plasmid carrying the gene for tetracycline resistance (Tet$^R$) transforms a host cell previously sensitive to tetracycline into one which is resistant to it. A host cell transformed by a plasmid is called a "transformant".

Phage or Bacteriophage—Bacterial virus many of which include DNA sequences encapsidated in a protein envelope or coat ("capsid").

Cloning Vehicle—A plasmid, phage DNA or other DNA sequence which is able to replicate in a host cell, characterized by one or a small number of endonuclease recognition sites at which its DNA sequence may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance. A cloning vehicle is also known as a vector.

Host—An organism which on transformation by a cloning vehicle enables the cloning vehicle to replicate and to accomplish its other biological functions, e.g., the production of polypeptides or proteins through expression of the genes of a plasmid.

Expression—The process undergone by a gene to produce a polypeptide or protein. It is a combination of transcription and translation.

Transcription—The process of producing mRNA from a gene.

Translation—The process of producing a protein or polypeptide from mRNA.

Promoter—The region of the DNA of a gene at which RNA polymerase binds and initiates transcription. A promoter is located before the ribosome binding site of the gene.

Ribosome Binding Site—The region of the DNA of a gene which codes for a site on mRNA which helps the mRNA bind to the ribosome, so that translation can begin. The ribosome binding site is located after the promoter and before the translational start signal of the gene.

Gene—A DNA sequence which encodes, as a template for mRNA, a sequence of amino acids characteristic of a specific polypeptide or protein. A gene includes a promoter, a ribosome binding site, a translational start signal and a structural DNA sequence. In the case of a secreted protein or polypeptide, the gene also includes a signal DNA sequence.

Expression Control Sequence—A DNA sequence in a cloning vehicle that controls and regulates expression of genes of the cloning vehicle when operatively linked to those genes.

Signal DNA Sequence—A DNA sequence within a gene for a polypeptide or protein which encodes, as a template for mRNA, a sequence of hydrophobic amino acids at the amino terminus of the polypeptide or protein, i.e., a "signal sequence" or "hydrophobic leader sequence" of the polypeptide or protein. A signal DNA sequence is located in a gene for a polypeptide or protein immediately before the structural DNA sequence of the gene and after the transitional start signal (ATG) of the gene. A signal DNA sequence codes for the signal sequence of a polypeptide or protein which (signal sequence) is characteristic of a precursor of the polypeptide or protein.

It is believed that only a portion of a signal sequence of a precursor of a protein or polypeptide is essential for the precursor of the protein or polypeptide to be transported through the cell membrane of a host and for the occurrence of proper clipping of the precursor's signal sequence to form the mature protein or polypeptide during secretion. Hence, the term "signal DNA sequence" means the DNA sequence which codes for the essential portion of the signal sequence of a precursor of a protein or polypeptide, produced within a host cell.

Structural DNA Sequence—A DNA sequence within a gene which encodes, as a template for mRNA, a sequence of amino acids characteristic of a specific mature polypeptide or protein, i.e., the active form of the polypeptide or protein.

In accordance with this invention, any cloning vehicle, that contains a bacterial or phage gene for a protein, a polypeptide or an RNA molecule or a DNA fragment of such a bacterial or phage gene, including a promoter of the bacterial or phage gene, and that can be cleaved to form a cleavage site after the promoter, can be utilized. Preferably, the cloning vehicle contains a bacterial or phage gene or a DNA fragment thereof which codes for an extra-cellular or periplasmic protein or polypeptide (i.e., a protein or polypeptide that is normally secreted from a host cell). Examples of such a gene include the gene for antibiotic resistance, e.g., the gene for penicillin resistance (i.e., penicillinase), the gene for chloramphenicol resistance, and the gene for tetracycline resistance, the gene for alkaline phosphatase, and the gene for bacterial ribonuclease. However, cloning vehicles containing other bacterial or phage genes or DNA fragments thereof can also be suitably utilized, such as the phage genes for the lactose operon promoter, beta-galactosidase (provided it is cleaved within its first few amino acids) and the phage lambda $P_L$, carried on a phage or plasmid.

Also in accordance with this invention, any DNA fragment of a non-bacterial and non-phage gene ("non-bacterial DNA fragment") can be inserted into the cleavage site in the cloning vehicle to form a hybrid gene, provided the non-bacterial DNA fragment:

(1) contains its gene's complete structural DNA sequence for the selected protein or polypeptide and its gene's signal DNA sequence, so that the non-bacterial DNA fragment codes for a precursor of the selected protein or polypeptide, including the signal sequence of the precursor; and (2) contains its gene's translational start signal if the cleavage site in the cloning vehicle is before or within the translational start signal of the bacterial or phage gene or the DNA fragment thereof.

Preferably, the non-bacterial DNA fragment, utilized, contains its gene's complete DNA sequence which codes for a precursor of a protein or polypeptide that is normally secreted from a host cell. Among the non-bacterial DNA fragments which preferably are utilized are those which code for a precursor of a eukaryotic cell protein, such as preproinsulin, preserum albumin, prehuman growth hormone, preparathyroid hormone, and preinterferon. However, other non-bacterial DNA fragments can also be utilized, such as those which code for precursors of viral proteins. Preferably, the non-bacterial DNA fragment, utilized, also contains its gene's stop signal.

In accordance with this invention, the specific location of the cleavage site in the cloning vehicle, into which the non-bacterial DNA fragment is inserted, is not critical for making the selected mature protein or polypeptide. In this regard, the cleavage site can be located anywhere in the cloning vehicle: (1) after the promoter of the bacterial or phage gene or the DNA fragment thereof, preferably after the ribosome binding site of the bacterial or phage gene or the DNA fragment thereof; and (2) before the end of the structural DNA sequence of the bacterial or phage gene or the DNA fragment thereof—provided that the bacterial or phage gene or the DNA fragment thereof codes for a protein or polypeptide that is normally secreted from a host cell. With a bacterial or phage gene or a DNA fragment thereof that codes for a protein or polypeptide that is normally not secreted from a host cell, the cleavage site can be before or within the gene's or its DNA fragment's translational start signal or shortly after, i.e., no more than approximately 40 nucleotides after, the gene's or its DNA fragment's translational start signal. With a bacterial or phage gene or a DNA fragment thereof that codes for a protein or polypeptide that is normally secreted from a host cell, the cleavage site can be before, within or after, preferably no more than approximately 60 nucleotides after, the gene's or its DNA fragment's translational start signal (i.e., the cleavage site preferably leaves no more than about 20 amino acids of the signal sequence of the bacterial or phage protein or polypeptide). In general, it is particularly preferred that the cleavage site be within or no more than approximately 40 nucleotides after the translational start signal of the bacterial or phage gene or the DNA fragment thereof—regardless of whether the bacterial or phage gene or the DNA fragment thereof codes for a normally secreted or normally non-secreted protein or polypeptide.

In accordance with this invention, the non-bacterial DNA fragment is inserted into the cleavage site, after the promoter of either the bacterial or phage gene or the DNA fragment thereof, so that there is, in order, in the resulting hybrid gene: the promoter of the bacterial or phage gene or the DNA fragment thereof; a translational start signal (either from the bacterial or phage gene or the DNA fragment thereof or from the non-bacterial DNA fragment); the signal DNA sequence of the non-bacterial DNA fragment; and the structural DNA sequence of the non-bacterial DNA fragment. Preferably, for most efficient expression of the selected protein or polypeptide, a ribosome binding site (either from the bacterial or phage gene or the DNA fragment thereof or from the non-bacterial DNA fragment) is provided in the hybrid gene between the promoter and the translational start signal. Moreover, if the non-bacterial DNA fragment is inserted after the translational start signal of a bacterial or phage gene or a DNA fragment thereof, the reading frame of the non-bacterial DNA fragment should be located in the reading frame defined by the translational start signal of the bacterial or phage gene or the DNA fragment thereof.

A selected protein or polypeptide can be secreted in high yields from a bacterial host, transformed with a cloning vehicle of this invention, without there being a hydrophobic leader sequence or any other chemical substituents, such as a f-met, on the secreted protein or polypeptide. The hydrophobic leader sequence and any other chemical substituents, which were present on the precursor of the selected protein or polypeptide as synthesized within the host, are cleaved from the selected protein or polypeptide. It is believed that this happens during secretion from the host.

The following Examples are intended to illustrate more fully the present invention. All temperatures are in degrees Celsius (°C.), and all percentages (%) are by weight. All solutions are aqueous, unless otherwise expressly stated. "ug" stands for micrograms, and "ul" stands for microliters.

In the Examples, the starting materials, buffers, cell media, and routine method steps were as follows. Where standard materials or steps were utilized, reference will be made (by number) to the following papers:

(1) Bolivar et al, *Gene* 2, 95–113 (1977)
(2) Villa-Komaroff et al, *P.N.A.S.* 75, 3727–3731 (1978)
(3) Johnsrud, *P.N.A.S.* 75, 5314–5318 (1978)
(4) Boyer et al, *J. Mol. Biol.* 41, 459–472 (1969)
(5) Bedbrook et al, *Cell* 9, 707–716 (1976)
(6) Reiner, *J. Bact.* 97, 1522–1523 (1969)
(7) Legerski et al, *Nucl. Acids Res.* 5, 1445–1464 (1978)
(8) Helling et al, *J. Vir.* 14, 1235–1244 (1974)
(9) Maxam et al, *P.N.A.S.* 74, 560–564 (1977)
(10) Maizel et al, *Methods in Vir.* 5, 179–246 (1970)
(11) Broome et al, *P.N.A.S.* 75, 2746–2749 (1978)
(12) Makula et al, *Diabetes* 18, 660–689 (1969)
(13) Kessler, *J. Immunol.* 115, 1617 (1975).

STARTING MATERIALS

Cloning Vehicles

The cloning vehicles used in the Examples were derived from a starting cloning vehicle which was the small plasmid pBR322 as constructed and described by (1). The cloning vehicles could all be cleaved at a Pst I restriction site within the gene for *Escherichia coli* (*E. coli*) penicillinase.

Non-Bacterial DNA Fragments for a Precursor of a Protein or Polypeptide

The non-bacterial DNA fragments used in the Examples were: a Pst-ended, poly-G tailed, cDNA copy of the DNA fragment of the gene for rat preproinsulin that was constructed and described by (2) and is hereinafter called "DNA fragment 19" (called "PI 19" by (2)); and a derivative of DNA fragment 19. The non-bacterial DNA fragments encode all but the translational start signal (ATG) and the first two codons of the gene for rat preproinsulin.

Bacterial Hosts

Four well known strains of *E. coli* K-12 were used in the Examples: MM294, described by (3); HB101, described by (4); FMA10/lambdacI$_{857}$ or "FMA 10", described by (5); and PR13 described by (6). The hosts were selected for the presence, within them, of a plasmid which codes for resistance to the antibiotic tetracycline, the gene for which resistance is also encoded on pBR322.

| BUFFERS | |
|---|---|
| Tris-sucrose buffer | 100 mM Tris-HCl (pH 8) and 20% sucrose |
| Triton lysis buffer | 0.3% Triton X-100, 150 mM Tris-HCl (pH 8), and 0.2 M EDTA (pH 8) |
| Tris-EDTA buffer ("TE buffer") | 10 mM Tris-HCl (pH 8) and 1 mM EDTA |
| BAL31 buffer | 20 mM Tris-HCl (pH 8), 12.5 mM MgCl$_2$, 12.5 mM CaCl$_2$, 0.2 M NaCl, and 1 mM EDTA (pH 8) |
| NET buffer | 50 mM Tris-HCl (pH 7.5), 5 mM EDTA, and 0.15 M NaCl |
| CELL MEDIA | |
| 2YT medium | 6 g Bacto-tryptone (Difco), 10 g yeast extract and 5 g NaCl per liter |
| Glucose minimal medium | 6 g Na$_2$HPO$_4$, 3 g KH$_2$PO$_4$, 0.5 g NaCl, and 1 g NH$_4$Cl per liter, to which is added 10 ml 20% glucose, 1 ml 1% Vitamin B$_1$ and 1.5 ml |
| S medium | 1 M MgSO$_4$ 2 g NH$_4$Cl, 6 g Na$_2$HPO$_4$, 3 g KH$_2$PO$_4$, 3 g NaCl, and 10 mg MgCl$_2$ per liter, to which is added 10 ml 20% glucose and 1 ml 1% Vitamin B$_1$. |

ROUTINE METHOD STEPS

Certain procedures were carried out repeatedly in the Examples. Unless otherwise specified, they were done exactly as follows each time that they were carried out:

Transformations

Cells of *E. coli* K-12, to be transformed with a plasmid, were grown in 2YT medium to an OD$_{550}$ of 0.5 to 1.0 (2.5 to 5×10$^8$ cells/ml). 2×10$^9$ cells were harvested by centrifugation in a Sorvall SS-34 rotor for 10 minutes at 5,000 rpm, and the cells were then incubated for 20 minutes on ice in 0.5 ml 50 mM Tris-HCl (pH 8) and 50 mM CaCl$_2$ to concentrate them. The concentrated cells were harvested as above and resuspended in 50 ul of a buffer of 50 mM Tris-HCl (pH 8) and 30 mM CaCl$_2$.

Up to 0.2 ug plasmid DNA was added to the mixture of cells and buffer, and the cells were incubated for 15 minutes on ice and then incubated for 3 minutes at 37° and for 10 minutes at room temperature (25°). The cell-buffer mixture was diluted to 2 ml with 2YT medium and incubated on a roller at 37° for 30 minutes. The transformed cells were selected by their tetracycline resistance in a conventional manner, i.e., either in liquid culture by the addition of 8 ml 2YT medium, containing 20 ug/ml tetracycline, or on plates by plating for single colonies on rich plates containing 2YT medium, 0.15% Bacto-agar (Difco) and 20 ug/ml tetracycline.

Amplifying Plasmids

Cells carrying a plasmid were grown with shaking at 37° in 1 liter 2YT medium to an OD$_{550}$ of 0.5 to 1.0. 3.4 ml of chloramphenicol (5 mg/ml in ethanol) were added, and shaking continued for 8 to 16 hours.

Isolating Plasmids

One or more liters of cells of *E. coli* K-12 were harvested by centrifugation at 5,000 rpm in a Sorvall GSA rotor and then resuspended in 5 ml Tris-sucrose buffer. The cells were incubated on ice for 5 minutes after each addition of: (1) 1 ml 5 mg/ml lysozyme (Sigma) in water; (2) 2 ml 0.25 M EDTA (pH 8); and (3) 2.5 ml 5 M NaCl. The cells were lysed with the addition of 1 ml 10% sodium dodecylsulfate ("SDS") and 25 ul 30% polyethylene glycol in 2 M NaCl, and the lysate was centrifuged for 1 hour in an IEC A-160 rotor at 27,000 rpm. Plasmid DNA was precipitated from the cleared supernatant with 0.6 volumes of isopropanol.

The precipitated plasmid DNA was purified by resuspending in 1 ml TE buffer and then centrifuging for 5 minutes in a clinical centrifuge to remove the insoluble protein precipitate. The supernatant was made 0.3 M in NaOAc, and then, the plasmid DNA was precipitated with addition of 3 volumes of ethanol, resuspended in 1 ml TE buffer, and extracted twice with an equal volume of phenol equilibrated in TE buffer. The plasmid DNA was precipitated with 3 volumes of ethanol, resuspended in 1 ml TE buffer, and digested for one hour at 50° with 100 ug/ml ribonuclease (Worthington Biochemical, N.J.). The plasmid DNA was extracted one more time with an equal volume of phenol, precipitated with 3 volumes of ethanol, resuspended in 50 mM NaOAc (pH 4) and extracted 2 to 3 times with equal volumes of phenol equilibrated in 50 mM NaOAc (pH 4) in a minor modification of the method described by 7). The plasmid DNA was then extracted once with an equal volume of ether, precipitated with 3 volumes of ethanol, and resuspended in ether to final concentration of 1 mg/ml.

For plasmid DNA from cell volumes of 1 to 25 ml at an $OD_{550}$ of 0.5 to 1.0, the cells were harvested as described above and purified by resuspending in 100 ul Trissucrose buffer as described above. The cells were then incubated on ice for 15 minutes with 5 mg/ml lysozyme in 20 mM EDTA (pH 8) and lysed with the addition of 850 ul Triton lysis buffer. The lysate was centrifuged in a Sorvall SA-600 rotor for 1 hour at 17,000 rpm. The plasmid DNA was then precipitated from the supernatant with isopropanol as described above, and the plasmid DNA precipitate was purified as described above.

Cutting or Cleaving Plasmids

Plasmids were cleaved with conventional restriction enzymes PstI, EcoRI, SalI, HinII and AvaII, purchased from New England Bio Labs, Waltham, Mass. The restriction enzymes were added to plasmids at conventional concentrations and temperatures and with buffers as recommended by New England Bio Labs.

Ligating DNA Fragments—Polymerization and Circulation

All DNA fragments were ligated at 15° in a ligation buffer of 25 mM Tris-HCl (pH 7.6), 10 mM $MgCl_2$, 10 mM dithiothreitol ("DTT"), and 100 uM adenosine triphosphate ("ATP").

The ligation procedure was carried out in two steps: polymerization and subsequent circularization. DNA fragments to be ligated to each other were polymerized in a 5 ul reaction volume with an amount of T4 DNA ligase (Bethesda Research Laboratories, Bethesda, Md.) sufficient for a complete reaction. The polymerized fragments were then circularized by dilution with ligation buffer to a 50 ul reaction volume and the addition of another aliquot of T4 DNA ligase, sufficient to complete the reaction.

Agarose Gel Electrophoresis 0.7% agarose gel electrophoresis for separating cut plasmid fragments, supercoiled plasmids, and DNA fragments 1000 to 10,000 nucleotides in length was performed exactly as described by (8).

Polyacrylamide Gel Electrophoresis

5% polyacrylamide gel electrophoresis for the separation of DNA fragments 100 to 4000 nucleotides in length was performed exactly as described by (9). 15% polyacrylamide gel electrophoresis for the separation of proteins of molecular weights of 5,000 to 20,000 was performed exactly as described by (10).

Gel Elution

DNA fragments were eluted from either polyacrylamide or agarose gel pieces exactly as described by (9).

DNA Sequencing

DNA fragments were either 540 or 3' end labeled, and their DNA sequences were determined exactly as described by (9).

P2 Containment

All work involving cells (including cell transformations, cell growth and cell fractionation) containing plasmids, cloned with DNA fragments of rat preproinsulin gene, was done under P2 containment in compliance with the revised N.I.H. guidelines for recombinant DNA research, published in the *Federal Register* 43, no. 247, 60,080–60,105 (Dec. 22, 1978).

EXAMPLES

Making Cloning Vehicles (II, IV and VI) From the Cloning Vehicle pBR322 (I) By Steps A to E, Shown in FIG. 1

Step A. Elimination of the HinII-SalI Site in pBR322 To Make the Penicillinase Gene HinII Site Unique The HinII-SalI site in the gene for tetracycline resistance (speckled in FIG. 1) in the plasmid pBR322 was eliminated to make the Hin II site in the penicillinase gene (black in FIG. 1) of the plasmid unique. pBR322 was mutagenized and amplified by growing the MM294 strain of *E. coli*, carrying pBR322, in 1 liter of 2YT medium, containing 3.4 ml of chloramphenicol to which was added 25 mg N-methyl-N'-nitro-N-nitrosoguanide, at 34° for 24–72 hours with shaking. The plasmid was isolated and then cut exhaustively with SalI. The cut plasmid fractions were used to transform MM294. MM294 cells with tetracycline resistance were selected, and the plasmid was isolated from the selected cells. The plasmid was then cut again exhaustively with SalI, used to transform MM294, and isolated from tetracycline resistant cells, as above, until a fraction resistance to SalI could be seen as supercoiled plasmids by agarose gel electrophoresis. These SalI resistant plasmids were isolated from single colonies and tested, using agarose gel electrophoresis, to make sure that they were resistant to cutting by both SalI and HinII. A single isolate, resistant to SalI and HinII, was then chosen as the plasmid (II) for the next step B in FIG. 1.

Step B. Cutting Plasmid (II) with HinII and Removing the Nucleotides Between the Cut Plasmid End and the Translational Start Signal (ATG) of the Penicillinase Gene.

The plasmid (II) from step A was cut with HinII to form the linear plasmid (III). The translational start signal (cross-hatched in FIG. 1) of the penicillinase gene was about 300 nucleotides from one HinII-cut end of the linear plasmid (III). The ends of 0.2 ug plasmid (III) were chewed back with 2 units of the exonuclease BAL31, described by (7), for 5 minutes at 15° in BAL31 buffer in a 20 ul reaction volume. The various resulting chewed back plasmids were then used for the next step C in FIG. 1.

Step C. Insertion of a Pst Linker (G Pst C) at One of the Chewed Back Ends of Plasmid (III) and Circularization of the Resulting Plasmids to Produce Plasmids (IV), Each with a Pst Restriction Site Near the Translational Start Signal of the Penicillinase Gene.

0.2 ug chewed back plasmids were polymerized for 2 hours with T4 DNA ligase to 0.2 ug Pst linker (Collaborative Research, Bethesda, Md.), and then the 5' end of each chewed back plasmid with a ligated linker was kinased in the presence of ATP and polynucleotide kinase in the manner described by 9). The sequence of the Pst linker was 5'-GCTGCAGC-3', where CTGCAG defines the site of cutting by PstI; the bases which came from the Pst linker are in italics in FIGS. 2 and 3. The chewed back plasmids with ligated linkers were circularized for 5 hours. The various resulting plasmids (IV) were transformed into MM294, and the MM294 cells were selected for tetracycline resistance in liquid culture.

Step D. Isolation of DNA Fragments (V) with Pst Restriction Sites Near the Translation Start Signal of the Penicillnase Gene.

The various plasmids (IV), each with a Pst linker inserted in step C somewhere near the translation start signal of the penicillinase gene, were amplified in MM294, isolated from 10 mls of amplified cells, and then cut with the restriction enzymes EcoRI and PstI. The translational start signal of each plasmid (IV) was about 200 nucleotides from the EcoRI site. Therefore, the DNA fragments from the cut plasmids (IV) were electrophoresed on a 5% polyacrylamide gel, and the various DNA fragments (V) containing approximately 150–300 nucleotides were identified using xylene cyanol as a die marker. The gel slice containing the DNA fragments (V) of approximately 150–300 nucleotides were eluted and used for the next step E in FIG. 1.

Step E. Ligating DNA Fragments (V) Back into pBR322.

pBR322 was cut with both EcoRI and PstI, and the large fragment containing the gene for resistance to tetracycline was isolated by 0.7% agarose gel electrophoresis. 0.2 ug of the large pBR322 fragment was ligated to 0.2 ug DNA fragments (V) by polymerizing for 2 hours and then circularizing for 5 hours to form the cloned plasmids (VI). To separate the various cloned plasmids (VI), containing various DNA fragments (V) of differing lengths, the cloned plasmids (VI) were transformed into MM294 and then were selected on plates. In this regard, transformed MM294 cells were plated for single colonies, single colonies were picked at random, and each separate plasmid was isolated from 5 ml of cells of each single colony. The plasmids were each cut with AvaII, 3'-end labeled with 20 uM deoxyguanosine triphosphate and 2 uM alpha-$^{32}$p-adenosine triphosphate in the manner described by (9), cut with EcoRI, and sequenced across the Pst site in the manner described by (9). Two cloned plasmids (VI), i.e., "pKT241" of FIG. 2 and "pKT218" of FIG. 3, were isolated and characterized in this way and then used as the cloning vehicles (VI) in the Examples. FIGS. 2 and 3 show the DNA sequences and the amino acid sequences they encode for the EcoRI-PstI fragments (V), ligated on to a fragment of the penicillinase gene of pBR322, to make the pKT241 and pKT218 cloning vehicles (VI). These cloning vehicles each comprise an altered penicillinase gene, with a Pst restriction site that is 4 (in the case of pKT218) or 12 (in the case of pKT241) codons from the translational start signal of the penicillinase gene.

Making the Non-Bacterial DNA Fragments to Be Cloned into the Cloning Vehicles (VI)

FIG. 4 shows the DNA sequence of the 5' end of non-bacterial DNA fragment 19, isolated and sequenced by (2). DNA fragment 19 is a Pst-ended, poly-G tailed, cDNA copy of a fragment of the gene for rat preproinsulin. DNA fragment 19 contains the signal DNA sequence and the structural DNA sequence of the gene for rat preproinsulin, as well as the stop signal (TGA) at the gene's 3' end. The amino acid sequence, for which this DNA fragment codes, has also been indicated in FIG. 4. The amino acids in italics in FIG. 4 are amino acids coded for by the poly-G tail and the Pst site. The DNA fragment 19 of FIG. 4 contains all but the first three codons of the rat preproinsulin gene. The end of the signal sequence and the start of the proinsulin, for which the DNA fragment codes, are indicated by an arrow before amino acid +1.

FIG. 5 shows the DNA sequence and the amino acid sequence, which it encodes, of the 5' end of another non-bacterial DNA fragment "CB6" of the gene for rat preproinsulin. DNA fragment CB6 was made by incubating 0.2 ug DNA fragment 19 with 2 units of the exonuclease BAL31, described by (7), in 150 ul BAL31 buffer for 45 seconds at 15°. The chewed back DNA fragments were polymerized for 2 hours with T4 DNA ligase to 0.2 ug Pst linker and electrophoresed on a 5% polyacrylamide gel. DNA fragments about 40 nucleotides smaller than DNA fragment 19 were eluted, cut with PstI and ligated to the Pst site of PstI-cut pBR322. The resulting plasmids were transformed into the HB101 strain of E. coli and selected on plates, as above. Selected single colonies of HB101 were cultured in 2YT medium to 5 ml. The plasmids were cut with AvaII, 3'-end labeled and sequenced across the Pst site, as above. Among the DNA fragments sequenced was DNA fragment CB6. The signal DNA sequence for rat preproinsulin of DNA fragment CB6 was found to be essentially identical to that of DNA fragment 19 but was read in a different frame from DNA fragment 19 and contained fewer G nucleotides, added by the poly-G tail.

Cloning the Non-bacterial DNA Fragments Into The Cloning Vehicles (VI) By Step F Shown In FIG. 1

Step F. Cloning DNA Fragment CB6 into Cloning Vehicle pKT218 and DNA Fragment 19 into Cloning Vehicle pKT241.

0.2 ug cloning vehicle pKT218 was cut with PstI. 0.2 ug PstI-cut pKT218 was polymerized to 0.2 ug of the Pst-ended DNA fragment CB6 for 2 hours, then circularized by dilution for 5 hours. The resulting cloned plasmid (VII), "pKT218.CB6", was transformed into the FMA10 strain of E. coli, selected on plates as above, and cultured at 34° in 2YT medium, supplemented with 40 ug/ml of thymidine.

Using the same procedure, 0.2 ug of DNA fragment 19 was cloned into 0.2 ug of cloning vehicle pKT241 to form the cloned plasmid (VII), "pKT241.19". The pKT241.19 plasmid was then transformed, selected on plates and cultured, as above.

To isolate FMA10 transformants with pKT218.CB6 or pKT241.19 cloned plasmids (VII) which contain the non-bacterial DNA fragment (CB6 or 19) in the correct orientation for reading from the promoter of the bacterial (penicillinase) gene, so that rat preproinsulin is produced in the transformants, single colonies of transformants, containing one of the cloned plasmids (pKT218.CB6 or pKT241.19), were picked on to replica plates containing 2YT medium, 0.15% Bacto-agar and 20 ug/ml tetracycline, plus 40 ug/ml thymidine. The transformants were grown at 34° and lysed on the plate by induction of their lambda phage at 42° for two hours. A two-site solid-phase radioimmunoassay on one of the replica plates was done exactly as described by 11), except that normal guinea pig serum, instead of normal rabbit serum, was used in the wash buffer. Cloned plasmids (pKT218.CB6 or pKT241.19) from each transformant, which tested positive for the presence of rat insulin antigen, were cloning vehicles (VII) and were transformed into a bacterial host, the strain PR13 of E. coli.

Culturing Bacterial Hosts Transformed With Cloning Vehicles (VII)

PR13 transformed with the pKT218.CB6 or pKT241.19 cloning vehicle (VII), expressing rat insulin antigen, was grown in 100 ml Glucose minimal medium supplemented with 2% cas(casein hydrolyzate) amino acids (Difco) to an OD550 of 0.2 to 0.4 at 37°.

Analysis of Protein Secreted by Cultured Hosts

Transformed PR13 host cells were harvested and then washed by being suspended in Tris-sucrose buffer. The washed cells were pelleted by centrifugation for 10 minutes at 5,000 rpm in a Sorvall SS-34 rotor. One portion of the cells was then lysed to release the contents of the whole cell. Another portion of the washed cells was fractionated into the contents of the periplasm and the contents of the cytoplasm plus the cell membrane.

Cells were lysed for their whole cell insulin antigen content by being resuspended in 100 ul Tris-sucrose buffer, incubated 15 minutes with 50 ul 5 mg/ml lysozyme in 20 mM EDTA and lysed with the addition of 850 ul Triton lysis buffer. The supernatant from a one hour centrifugation at 17,000 rpm in a Sorvall SA-600 rotor contained the whole cell insulin antigen.

Cells were fractionated by being resuspended in 900 ul Tris-sucrose buffer and incubated 15 minutes on ice with 100 ul 5 mg/ml lysozyme in 20 mM EDTA (pH 8). The cells were pelleted as before. The supernatant contained the contents of the cell periplasm, and the pellet contained the contents of the cytoplasm and cell membrane. After separating the supernatant for analysis of its insulin antigen content, the pellet was resuspended gently in 1 ml Tris-sucrose buffer, repelleted and resuspended with stirring, using a glass rod, in 100 ul Tris-sucrose buffer. The cells were lysed with Triton lysis buffer and centrifuged for 1 hour in a Sorvall SA-600 rotor at 17,000 rpm. The supernatant contained the contents of the cytoplasm and membrane of the cell.

Standard liquid radioimmunuassays were carried out, exactly as described by (12), to determine the insulin antigen content of each fraction obtained from the PR13 cells. Aliquots of cell fractions to be tested were preincubated with an amount of anti-insulin IgG sufficient to complex 75% of the input labelled insulin. The IgG fraction of guinea pig anti-insulin serum was used both in the liquid and the solid-phase radioimmunoassays and was prepared exactly as described by (11).

The Table, which follows, summarizes the results of culturing PR13 containing the pKT241.19 cloning vehicle (VII) and culturing PR13 containing the pKT218.CB6 cloning vehicle (VII) and shows that about 90% of the rat insulin antigen is found in the periplasmic space of the PR13 host cells.

TABLE

RAT INSULIN ANTIGEN CONTENT OF PR13 HOST CELLS CONTAINING pKT218.CB6 218.CB6 OR pKT241.19 CLONING VEHICLES (VII)
Rat Insulin Antigen Molecules In Cell

| Cloning Vehicle | Peri-plasm* of Cell | Cytoplasm & Membrane of Cell* | Total* | Whole Cell** | % In Peri-plasm* |
|---|---|---|---|---|---|
| pKT218.CB6 | — | — | — | 368 | — |
| pKT218.CB6 | 365 | 37 | 402 | — | 91% |
| pKT241.19 | — | — | — | 1555 | — |
| pKT241.19 | 1320 | 298 | 1618 | — | 82% |
| pKT241.19 | 1592 | 105 | 1697 | — | 94% |

*From fractionated cell contents.
**From whole cell contents.

Determining That Mature Protein Is Produced By Bacterial Hosts Transformed With Cloning Vehicles (VII)

5 ml of PR13 transformed with the pKT218.CB6 or pKT241.19 cloning vehicle (VII) were grown in S medium supplemented with 40 ug/ml leucine and 40 ug/ml threonine to an $OD_{550}$ of 0.3 and then incubated one-half to one hour with 5 mCi $H_2{}^{35}SO_4$ at 34°. Harvested cells were lysed for whole cell antigen content as described above, and the supernatant was incubated with 2 ul of an IgG fraction of guinea pig anti-porcine insulin serum, prepared as described by 11). 2 ul of this IgG fraction could bind about 300 ng of insulin antigen, and hence it was a 200-fold excess of antibody. After incubating for 3 hours at 37° and 3 hours on ice, the anti-insulin IgG-rat proinsulin complexes were immunoprecipitated as described by 13): 100 ul glutararaldehyde-treated Staph A (Staphylococcus aureus) bacteria in NET buffer (10% volume/volume) were added to the complexes and incubation continued another hour on ice.

The Staph A cells were pelleted by centrifugation at 10,000 rpm for 5 minutes in a Sorvall SS-34 rotor to remove the insulin antigen-antibody complexes from the supernatant. The cells were washed by being resuspended in 100 ul NET-NON buffer (NET buffer plus Nonidet P-40 detergent (Particle Data Labs, Inc., Elmhurst, Ill.), 1 mg/ml ovalbumin and 0.5 M NaCl). Then, another 900 ul of NET-NON buffer were added, and the cells were pelleted as before. This washing procedure was then repeated three more times. Two final washes were done in NET buffer, containing 0.5% Nonidet P-40 detergent, and then the cells were boiled 3 minutes in 50 ul Maizel gel loading buffer (containing SDS) as described by 10). The Staph A cells were pelleted again by centriguation as above.

The supernatant, containing denatured proteins (including radioactive proinsulin), were loaded on a 10×8×0.2 cm 15% Maizel gel exactly as described by 10). The gel was run at 40 volts for one-half hour and 110 volts for 4-5 hours, until the bromophenol blue tracking dye was at the bottom, and then autoradiographed for one hour on Kodak XR-5 film. The gel piece, comprising the predominant radioactive piece in the gel (as seen from the film) and containing the radioactive proinsulin, was cut from the gel, ground up with a glass rod and eluted at room temperature for 8 hours in 50 mM ammonium bicarbonate (pH 7.5), 0.2 mg/ml ovalbumin (Sigma) as a carrier protein for elution, 0.1%

SDS, and 0.2 mM DTT. The crushed gel was removed by filtration through glass wool, and the protein was lyophilized to dryness. The protein was resuspended in 100 ul water and precipitated with 5 volumes of acetone.

The protein was resuspended in 200 ul 70% formic acid, to which was added 3 mg ovalbumin as a carrier protein for sequencing and 3 mg Polybrene (Aldrich) in 200 ul 70% formic acid to help bind the protein to the sequenator cup. The protein was loaded onto a Beckman Sequenator, updated model 860C, and each cycle was run with a 0.1 M Quadrol buffer (Beckman) and the appropriate Sequenator program. An amino acid derivative of the protein was collected after each cycle and dried under streaming nitrogen in a 37° bath. Resuspension in 200 ul 0.1 N HCl and incubation at 80° for 10 minutes converted each unstable derivative to a stable derivative. 20-100 ul of each stable derivative were added to 2 ml Aquasol (New England Nuclear, Boston, Mass.), and the radiation of each derivative was determined by liquid scintillation.

The liquid scintillation counts per minute were plotted against amino acid position for the protein from each cultured PR13 host, containing either the pKT241.19 or pKT218.CB6 cloning vehicle (VII). In nature, mature proinsulin has the sulfur containing amino acid, cysteine, at positions 7 and 19 along its amino acid chain. The plot showed the quantitative recovery of radioactive sulfur at positions 7 and 19 along the amino acid chain of the proinsulin produced by each cultured PR13 host. This proved that mature proinsulin had been produced by each PR13 host, containing the pKT218.CB6 cloning vehicle or the pKT241.19 cloning vehicle.

It is considered that the invention and many of its attendant advantages will be understood from the foregoing description and that it will be apparent that various changes may be made in the steps of the described method for mature protein synthesis without departing from the spirit and scope of the invention or sacrificing all of its material advantages, the method hereinbefore described being merely a preferred embodiment.

We claim:

1. A method of synthesizing within a bacterial host, and secreting through the membrane of the bacterial host, a selected mature protein or polypeptide, which comprises:
(a) cleaving a cloning vehicle, comprising a plasmid, phage DNA or other DNA sequence which is able to replicate in the bacterial host, to form a cleavage site after a promoter of either (1) a bacterial or phage gene within the cloning vehicle or (2) a DNA fragment of the bacterial or phage gene;
(b) forming a hybrid gene by inserting into the cleavage site a non-bacterial DNA fragment which codes for a precursor of the selected protein or polypeptide, including the signal sequence of the selected protein or polypeptide;
(c) transforming the bacterial host with the cloning vehicle; and then
(d) culturing the transformed bacterial host to secrete the selected protein or polypeptide.

2. The method of claim 1 wherein the bacterial or phage gene or the DNA fragment thereof codes for a normally secreted protein or polypeptide and the cleavage site is before, within or no more than approximately 60 nucleotides after the translational start signal of the bacterial or phage gene or the DNA fragment thereof.

3. The method of claim 1 wherein the bacterial or phage gene or the DNA fragment thereof codes for a normally non-secreted protein or polypeptide and the cleavage site is before, within or no more than approximately 40 nucleotides after the translational start signal of the bacterial or phage gene or the DNA fragment thereof.

4. The method of claims 2 or 3 wherein the cleavage site is within or no more than approximately 40 nucleotides after the translational start signal of the bacteria or phage gene or the DNA fragment thereof.

5. The method of claim 1 wherein a DNA fragment of the *E. coli* penicillinase gene is cleaved.

6. The method of claim 5 wherein the cloning vehicle is derived from the plasmid pBR322.

7. The method of claim 1 wherein the non-bacterial DNA fragment codes for preproinsulin, preserum albumin, prehuman growth hormone, preparathyroid hormone, or preinterferon.

8. A cloning vehicle, comprising a plasmid, phage DNA or other DNA sequence which is able to replicate in a bacterial host and comprising in order:
a promoter of a bacterial or phage gene;
a translation start signal; and
a non-bacterial DNA fragment which codes for a precursor of a protein or polypeptide, including the signal sequence of the protein or polypeptide; the reading frame of the non-bacterial DNA fragment being located in the reading frame define by the translational start signal.

9. The cloning vehicle of claim 8 which further includes a ribosome binding site between the promoter and the translational start signal.

10. The cloning vehicle of claim 9 wherein the promoter is the promoter of the *E. coli* penicillinase gene.

11. The cloning vehicle of claim 9 which further includes no more than approximately 40 nucleotides of the bacterial or phage gene after the translational start signal and before the non-bacterial DNA fragment.

12. The cloning vehicle of claim 9 wherein the non-bacterial DNA fragment codes for preproinsulin, preserum albumin, prehuman growth hormone, preparathyroid hormone, or preinterferon.

13. A bacterial host transformed with a cloning vehicle, the cloning vehicle comprising a plasmid, phage DNA or other DNA sequence which is able to replicate in the bacterial host and comprising in order:
a promoter of a bacterial or phage gene;
a translational start signal; and
a non-bacterial DNA fragment which codes for a precursor of a protein or polypeptide, including the signal sequence of the protein or polypeptide; the reading frame of the non-bacterial DNA fragment being located in the reading frame defined by the translational start signal.

14. The host of claim 13 which further includes a ribosome binding site between the promoter and the translational start signal.

15. The host of claim 14 wherein the non-bacterial DNA fragment codes for preproinsulin, preserum albumin, prehuman growth hormone, preparathyroid hormone, or preinterferon.

16. A method of synthesizing within a bacterial host, and secreting through the membrane of the bacterial host, a selected mature protein or polypeptide, which comprises culturing the bacterial host; the bacterial host being transformed with a cloning vehicle, comprising a plasmid, phage DNA or other DNA sequence which is able to replicate in the bacterial host and comprising in order:

a promoter of a bacterial or phage gene;

a translational start signal; and a non-bacterial DNA fragment which codes for a precursor of the selected protein or polypeptide, including the signal sequence of the selected protein or polypeptide; the reading frame of the non-bacterial DNA fragment being located in the reading frame defined by the translational start signal.

17. The method of claim 16 wherein the cloning vehicle further includes a ribosome binding site between the promoter and the translational start signal.

18. The method of claim 17 wherein the promoter is the promoter of the *E. coli* penicillinase gene.

19. The method of claim 17 wherein the cloning vehicle further includes no more than approximately 40 nucleotides of the bacterial or phage gene after the translational start signal and before the non-bacterial DNA fragment.

* * * * *